United States Patent
Bubb

(10) Patent No.: US 6,840,960 B2
(45) Date of Patent: Jan. 11, 2005

(54) POROUS IMPLANT SYSTEM AND TREATMENT METHOD

(76) Inventor: Stephen K. Bubb, 1257 Huntington Dr., Kansas City, MO (US) 64113

( * ) Notice: Subject to any disclaimer, the term of this patent is extended or adjusted under 35 U.S.C. 154(b) by 124 days.

(21) Appl. No.: 10/260,149

(22) Filed: Sep. 27, 2002

(65) Prior Publication Data

US 2004/0064192 A1 Apr. 1, 2004

(51) Int. Cl.⁷ .................................................. A61F 2/28
(52) U.S. Cl. .................................................... 623/23.5
(58) Field of Search .............................. 623/23.5, 23.76, 623/23.75, 23.51, 23.56, 23.57; 606/198, 201, 202, 203, 204, 215; 604/317; 424/424, 423, 425; 433/173, 175

(56) References Cited

U.S. PATENT DOCUMENTS

| | | | |
|---|---|---|---|
| 5,522,901 A | | 6/1996 | Thomas et al. |
| 5,580,353 A | | 12/1996 | Mendes et al. |
| 5,716,360 A | | 2/1998 | Baldwin et al. |
| 5,738,686 A | | 4/1998 | Kubein-Meesenburg |
| 5,876,359 A | * | 3/1999 | Bock et al. .................. 601/150 |
| 5,958,314 A | * | 9/1999 | Draenert ...................... 264/42 |
| 6,051,016 A | * | 4/2000 | Mesaros et al. ............. 606/202 |
| 6,087,553 A | * | 7/2000 | Cohen et al. ............. 623/22.21 |
| 6,146,423 A | | 11/2000 | Cohen et al. |
| 6,159,246 A | | 12/2000 | Mendes et al. |
| 6,190,391 B1 | | 2/2001 | Stubbs |
| 6,344,061 B1 | * | 2/2002 | Leitao et al. ............... 623/23.5 |
| 6,355,215 B1 | | 3/2002 | Poggie et al. |
| 6,377,653 B1 | | 4/2002 | Lee et al. |
| 6,394,948 B1 | * | 5/2002 | Borst et al. .................... 600/37 |
| 6,430,427 B1 | | 8/2002 | Lee et al. |
| 2002/0143403 A1 | * | 10/2002 | Vaidyanathan et al. .. 623/23.51 |
| 2004/0039415 A1 | * | 2/2004 | Zamierowski ............... 606/215 |

* cited by examiner

Primary Examiner—Pedro Philogene
(74) Attorney, Agent, or Firm—Mark E. Brown

(57) ABSTRACT

A porous implant system includes a gradient source adapted for transferring a gradient to an interface connected to an implant at a patient situs. The gradient source is controlled by a programmable controller. The implant is bonded to the patient by tissue ingrowth, which is facilitated by the gradient formed across the porous portion of the implant. A treatment method and includes the steps of providing a porous implant, connecting same to a gradient source through an interface, forming a gradient across the implant and controlling the operation of the gradient source according to a predetermined and preprogrammed treatment protocol.

20 Claims, 13 Drawing Sheets

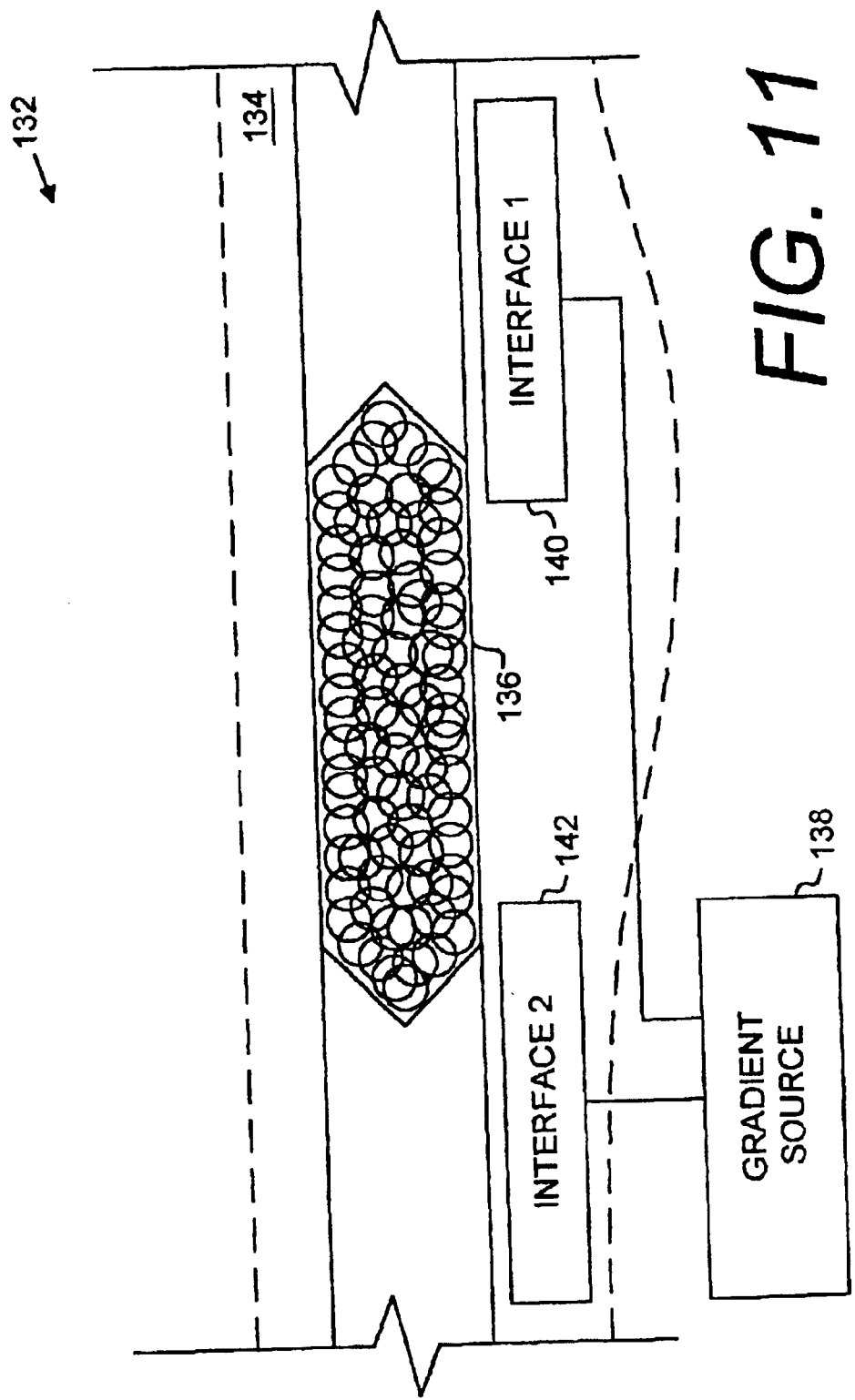

POROUS IMPLANT SYSTEM AND TREATMENT METHOD

BACKGROUND OF THE INVENTION

1. Field of the Invention

The present invention relates generally to implants, and in particular to a porous implant system and treatment methodology for both orthopedic and soft tissue applications, which promotes tissue interdigitation and healing.

2. Description of the Prior Art

In the medical, dental and veterinary fields, implants are in widespread use for treating a variety of patient conditions. For example, in the field of orthopedics, joints are commonly replaced with implants after the original joints fail through degeneration, trauma and other causes. Such implants are typically designed to promote bone induction, bone replacement and soft tissue anchoring. Porous materials have been extensively used in the manufacture of joint prostheses for this purpose. Their open-lattice configurations tend to promote interdigitation, tissue ingrowth and tissue outgrowth whereby integration with the patients' living tissues can occur.

Trabecular metal comprises a type of porous material, which is commonly used in orthopedic procedures. An example of such an implant is described in U.S. Pat. No. 5,456,723 entitled "Metallic Implant Anchorable to Bone Tissue for Replacing a Broken or Diseased Bone". Porous thermoplastic materials have also been used for orthopedic implants. Examples are described in U.S. Pat. No. 4,164,794 and No. 4,756,862, both of which are entitled "Prosthetic Devices Having Coatings of Selected Porous Bioengineering Thermoplastics". U.S. Pat. No. 5,443,512 for "Orthopedic Implant Device" and No. 6,087,553 for "Implantable Metallic Open-Celled Lattice/Polyethylene Composite Material and Devices" both describe orthopedic implants with metal and plastic composite constructions. All of these patents are incorporated herein by reference.

Trabecular metal and other porous implant materials, including thermoplastics, can promote tissue ingrowth under certain conditions. However, the depth of penetration of bone and soft tissue ingrowth may be limited by various biological factors. Moreover, depth and quality of tissue penetration, and the physical properties of the host/prosthesis interface, may be limited by both pathological and physiological host factors.

Another persistent problem with such implants relates to the potential for infection. Porous materials tend to encourage tissue ingrowth, but they can also accommodate microbes and metabolic agents. Digitization and integration can be hindered by the presence of toxins, wound drainage fluid and other substances, particularly when they are trapped in the porous material and closed within a surgery site after a medical procedure.

Artificial joints, implants and other prostheses are further susceptible to persistent problems with secure bonding to patients' living tissue. Macro and micro motion in such connections can compromise replacement joints and cause their premature failure. In order to strengthen such connections, adhesives and cements have been developed for bone-to-implant bonds. Such adhesives and cements can be combined with antibiotic and antimicrobial agents. For example, ALAC identifies an acrylic cement loaded with antibiotic or antimicrobial agents (ABX). Polymethylenemethacralate (PMMA) cement is also used for this purpose. However, problems can be encountered with inducing such cements into the voids and latticework formed in the porous implant materials.

In the related fields of chronic wound care and post-operative incision healing, gradients of various kinds have been utilized. For example, thermodynamic (temperature) gradients can stimulate cell growth. Electrical, gravitational and magnetic fields have also been utilized for this purpose. Considerable research is currently being directed toward the use of biologics in various medical applications. Gradients can be established with biological agents for enhancing healing and countering infection. Pressure differentials and gradients have been applied to close separated tissue portions and promote their healing. Negative pressure gradients have been used to apply suction forces for draining bodily fluids and exudates. Positive pressure gradients have been used to irrigate wound sites and infuse them with pharmacological agents, such as antibiotics, growth factors, etc.

The present invention combines concepts from the porous implant field with gradient formation equipment and treatment protocols to promote tissue ingrowth for anchoring implants. Forming a gradient at a situs also facilitates drainage and the application of biologics, such as antibiotics, growth factors and other fluids for controlling infection and promoting healing.

The design criteria for implants include secure connections with living tissue, facilitating tissue ingrowth, infection resistance and permanency. Another design objective is applicability to a wide range of procedures, including prosthetic fixation, cosmetic and structural bone substitution, treatment of failed bone unions, bone defects, composite tissue defects and other conditions. Heretofore there has not been available a porous implant system and treatment method with the advantages and features of the present invention.

SUMMARY OF THE INVENTION

In the practice of the present invention, a porous implant system and treatment method are provided for various conditions, including orthopedic procedures such as total joint replacement (TJR). The system and method involves the application of a gradient to a porous implant material. The gradient can be formed with a wide variety of different forces and influences. A negative pressure differential creates a suction force across the implant whereby tissue ingrowth is encouraged. The negative pressure differential/suction mode of operation also functions to drain the implant situs and remove toxins, microbes and metabolic agents. In a positive pressure/infusion mode, various biologic and pharmacological agents can be infused throughout the implant and the patient situs for countering infection, promoting tissue growth, etc. An interface, such as a tube, a sponge or a membrane, is provided for connecting the porous material of the implant to a pressure differential source.

BRIEF DESCRIPTION OF THE DRAWINGS

FIG. 11 is a cross-sectional view of the porous implant system applied to a tibia.

DETAILED DESCRIPTION OF THE PREFERRED EMBODIMENTS

Figure 1:
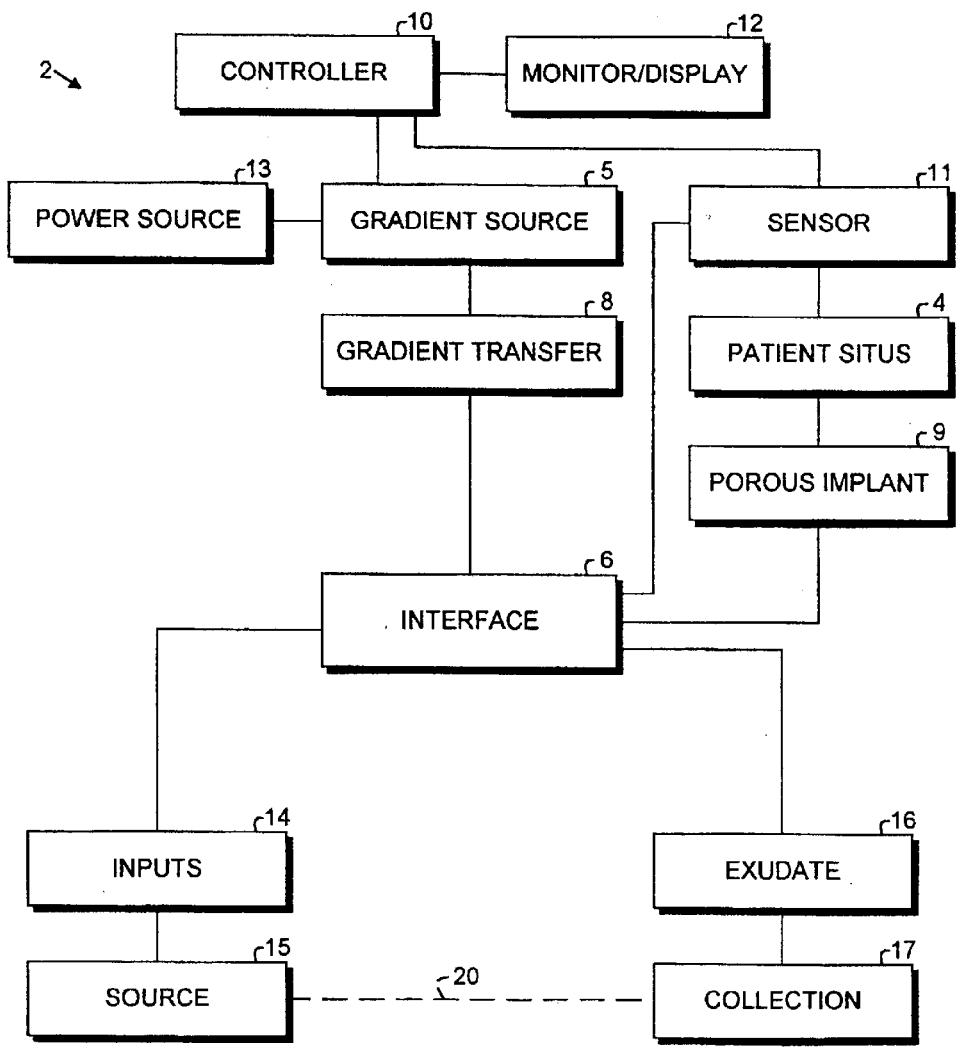
FIG. 1 is a block diagram of the porous implant system embodying the present invention.

I. Introduction and Environment.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. The words "inwardly" and "outwardly" will refer to directions toward and away from, respectively, the geometric center of the embodiment being described and designated parts thereof. Said terminology will include the words specifically mentioned, derivatives thereof and words of a similar import.

Referring to the drawings in more detail, the reference numeral 2 generally designates a porous implant pressure differential system embodying the present invention. The system 2 interacts with a patient situs 4 through a porous implant 9, which is connected to an interface 6. The interface 6 is connected to a gradient source 5 through a gradient transfer 8. The gradient source 5 is controlled by a controller 10, which provides output to a monitor/display 12 and is powered by a power source 13. Inputs 14 communicate with the patient situs 4 through the interface 6, and exudate 16 is drawn therefrom to a collection receptacle 18. Reperfusion of the patient's bodily fluids can occur along dashed line 20.

Without limitation on the generality of useful applications of the system 2, it can be applied to both human and animal patients and subjects in connection with a wide variety of medical, dental and veterinary conditions and treatments. For example, total joint replacements (TJRs) typically involve several procedures, which can benefit from the system 2. It will be appreciated that the system and treatment method of the present invention are applicable to a wide range of medical, dental and veterinary procedures and conditions.

Figure 2A:
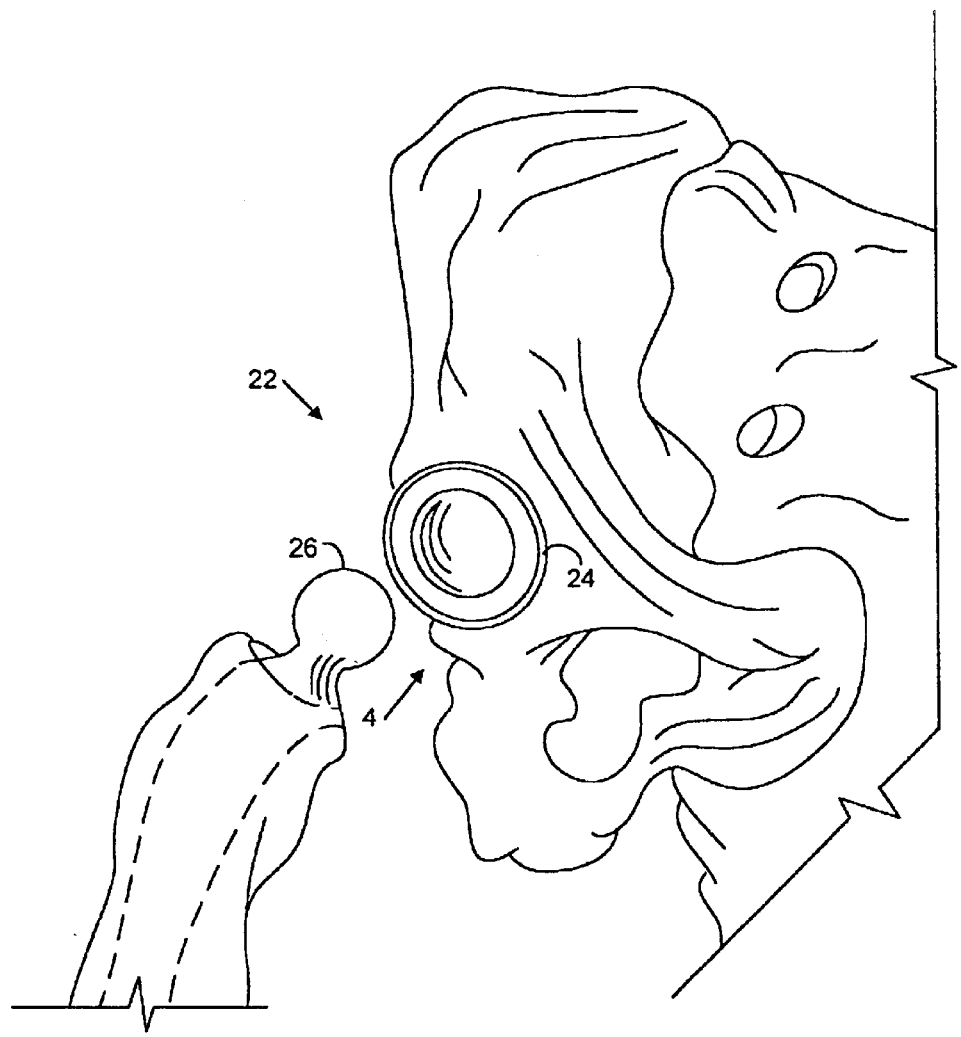
FIG. 2a is a perspective view of a total hip replacement (THR) procedure.
Figure 2B:
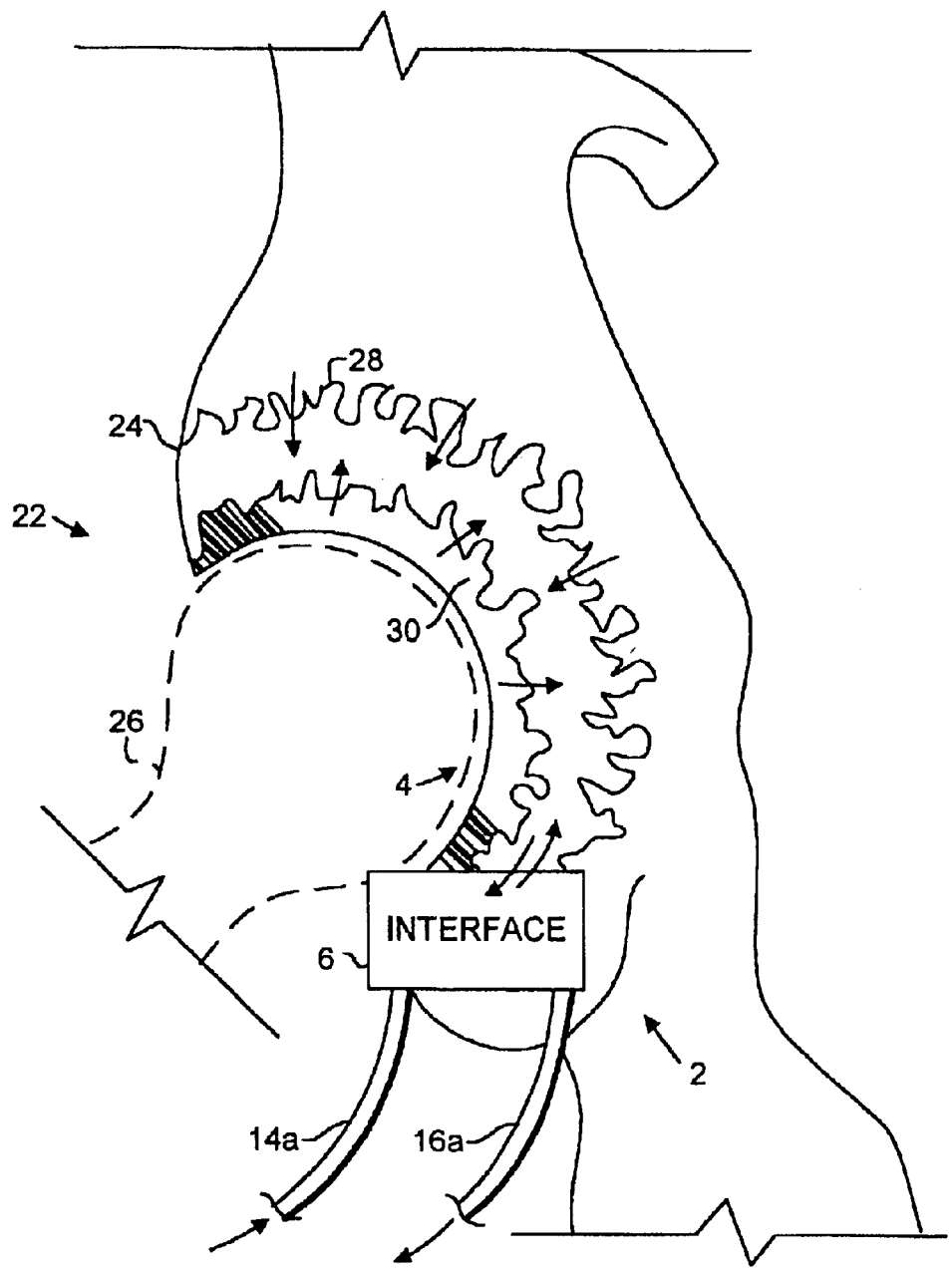
FIG. 2b is a cross-sectional view of a porous acetabular cup for the THR procedure.

A total hip replacement (THR) 22 is shown in FIGS. 2a, 2b and includes an acetabular cup assembly 24 and a femoral prosthesis 26. As shown in FIG. 2b, the acetabular cup assembly 24 includes a porous component 28 and a bearing or wear component 30, which can comprise a material such as polyethylene. Composite metal and plastic acetabular cups of this type are available from the Implex Corporation of Allendale, N.J.

The porous component 28 functions to distribute the pressure differential from the gradient source 5 through input and output lines (e.g., tubes, wires, etc.) 14a, 16a connected to an interface 6. The lines 14a, 16a function as gradient transfers (8 in FIG. 1). In a negative pressure/suction mode, the porous implant system 2 facilitates tissue interdigitation for enhancing and expediting bonding with the patient. Preferably, both tissue ingrowth into the porous component 28 and outgrowth onto same are enhanced. Moreover, in a negative pressure mode, various pharmacological agents and biologics, such as antibiotics, growth factors, etc., can be drawn into the porous component 28 for expediting healing, reducing infection, etc. In a negative pressure gradient (suction) mode, fluid, toxins, microbes and metabolic products can be drained from the situs 4. The risks of infection can thus be reduced and healing promoted by applying a pressure differential or other gradient to the porous component 28. Interdigitized tissue and pharmacological agents drawn and/or injected into the situs 4 by a negative and/or positive pressure differential across same will tend to displace bodily fluids and toxins occupying the interstitial spaces in the porous implant, thus reducing or eliminating an environment in which microbes and metabolic products can develop and infect the situs 4.

In a positive pressure/input mode the porous material 28 acts as a manifold to distribute the fluid input throughout the situs 4. It will be appreciated that the controller 10 can be programmed to alternate between these functions. Moreover, they can occur simultaneously as the system 2 provides a fluid input at one side of the porous component 28 and exudate is drained from the other side thereof.

The gradient source 5 and the interface 6 can comprise, for example, components of a vacuum assisted closure (VAC) system and interface from Kinetic Concepts, Inc. of San Antonio, Tex. For example, the interface 6 can comprise various suitable sponge materials, or can comprise a length of tubing attached to the porous component 28.

Figure 3:
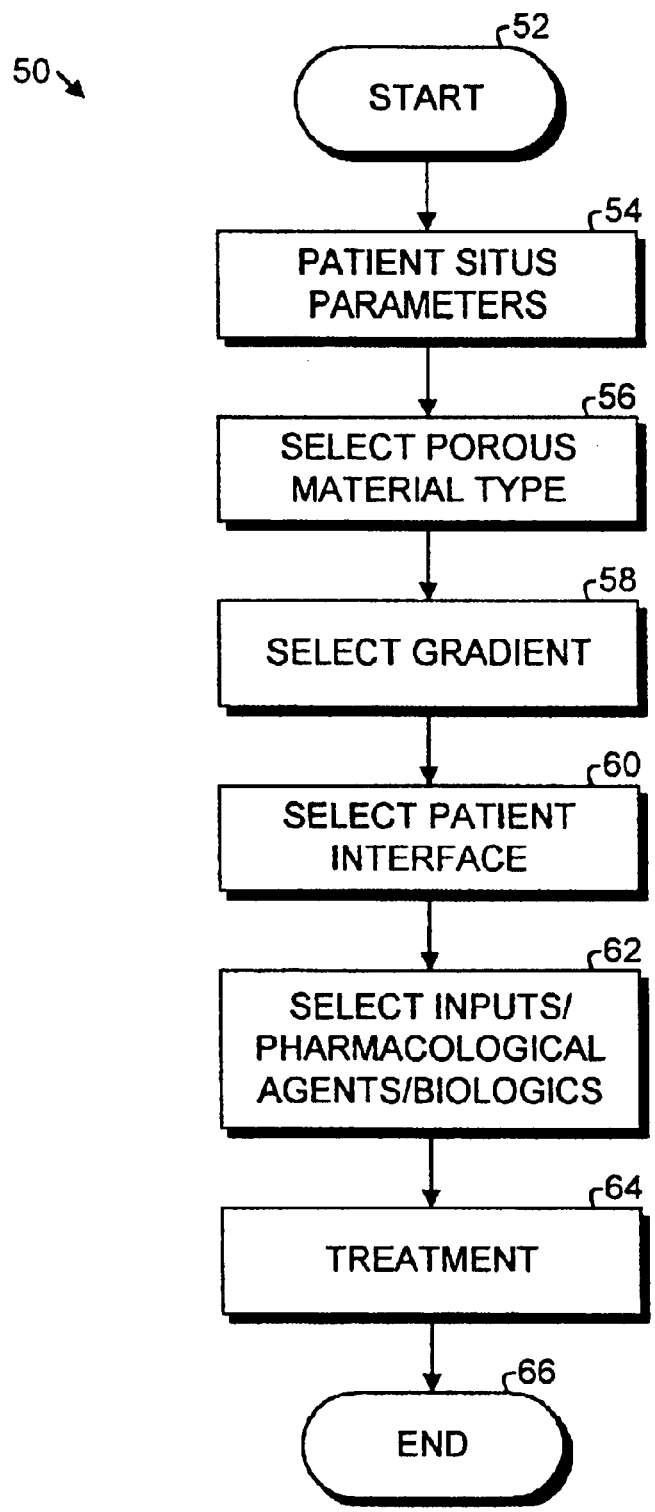
FIG. 3 is a flowchart of a porous implant treatment procedure according to the method of the present invention.

FIG. 3 is a flowchart showing an overview of a treatment method 50 of the present invention, utilizing the system 2 embodying the present invention. The process starts at 52 and proceeds to a patient situs parameters subprocedure 54. A porous material type is selected at 56, a gradient is selected at 58, a patient interface is selected at 60 and inputs/pharmacological agents/biologics are selected at 62. A treatment subprocedure occurs at 64 whereafter the methodology ends at 66. These subprocedures will be discussed below.

Figure 4:
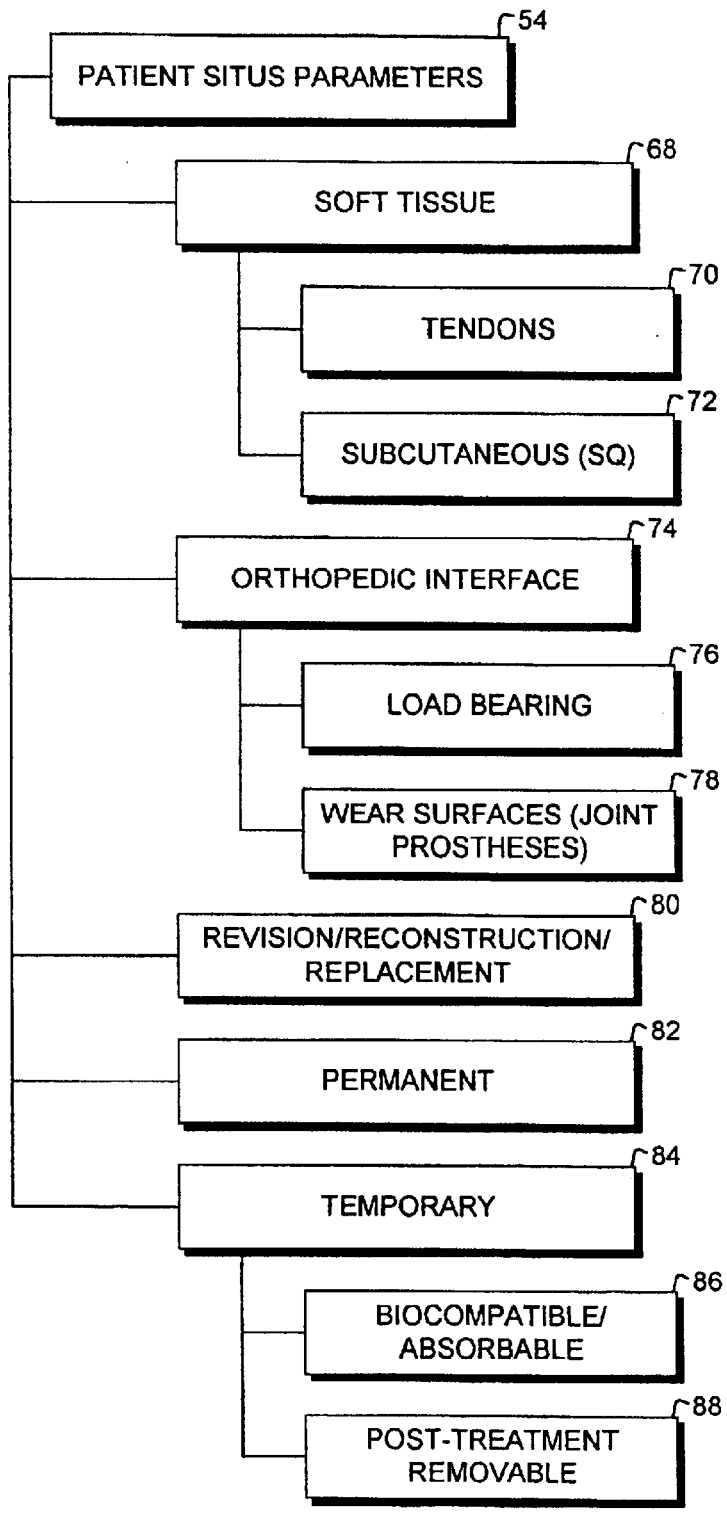
FIG. 4 is an outline of a subprocedure of the treatment method, which subprocedure involves patient situs parameters.

FIG. 4 is an outline of the patient situs parameter considerations 54. For soft tissue applications 68, the system 2 is adapted for connecting tendons and joining separated tissue at the subcutaneous (SQ) layer of the patient at 70, 72 respectively. For example, a pair of porous material components 28 can be placed against soft tissue portions and bonded to same with tissue interdigitation. The porous material components 28 can then be mechanically drawn together for closure of the separated tissue portions. In an orthopedic interface 74, such as the hip replacement discussed above, different considerations are taken into account if the situs is load bearing or not (76), and depending upon whether it includes wear surfaces (78), for example, in connection with a joint prosthesis. The situs 4 can comprise a diseased or damaged tissue location whereat a revision or reconstruction is performed at 80. In orthopedic medicine, previous implants and prostheses are commonly replaced due to their failure, infection, ineffectiveness, etc. The system and method of the present invention can be used to advantage in such implant extraction and replacement procedures.

The interface 6 can comprise either permanent (82) or temporary components (84), or both. For example, biocompatible and absorbable components are designed to dissolve within the patient at 86. By encouraging living tissue interdigitation, the system 2 can enhance the absorption of the interface 6 components. Their components are designed for removal. For example, the interface 6 can include tubing adapted for placement upon installation of the system 2. After the system 2 has accomplished its purpose, such as draining a wound, applying and distributing biologics, etc., removable components can be extracted at 88.

Figure 5:
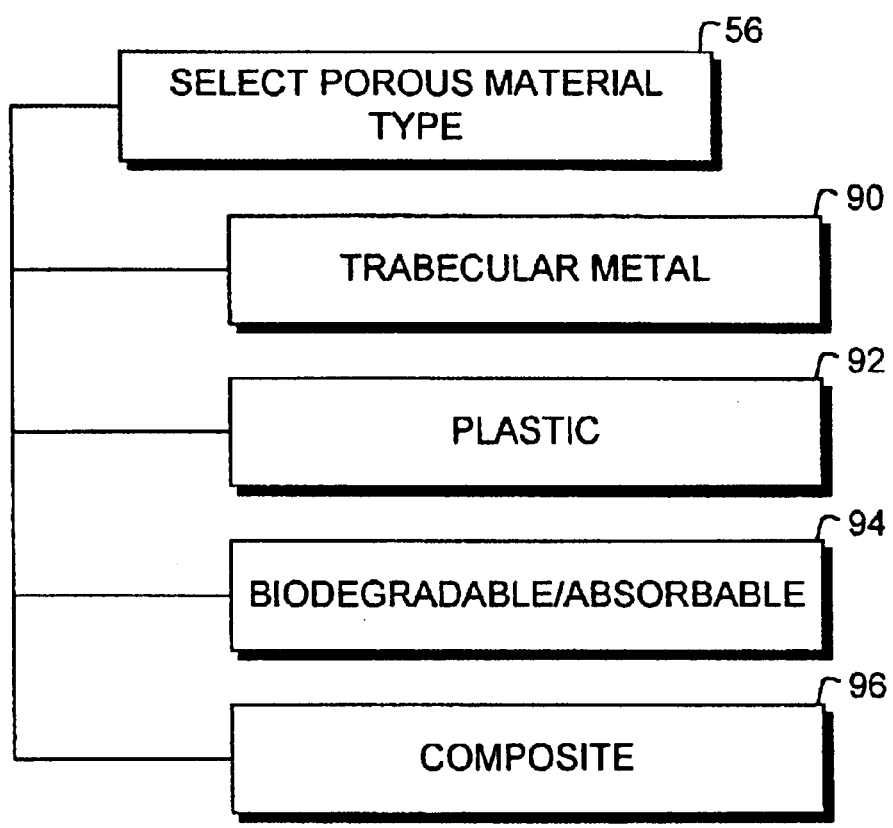
FIG. 5 is an outline of a subprocedure of the treatment method, which subprocedure involves selecting a porous material type.

FIG. 5 shows the subprocedure 56 for selecting a porous material. Trabecular metal is shown at 90. Porous thermoplastic materials (92) are also suitable for receiving tissue ingrowth and would benefit from a pressure differential. Moreover, biodegradable and absorbable porous materials (94) can be utilized for eventual absorption into the patient through replacement by the patient's living tissue. A composite material composition can be selected at 96.

Figure 6:
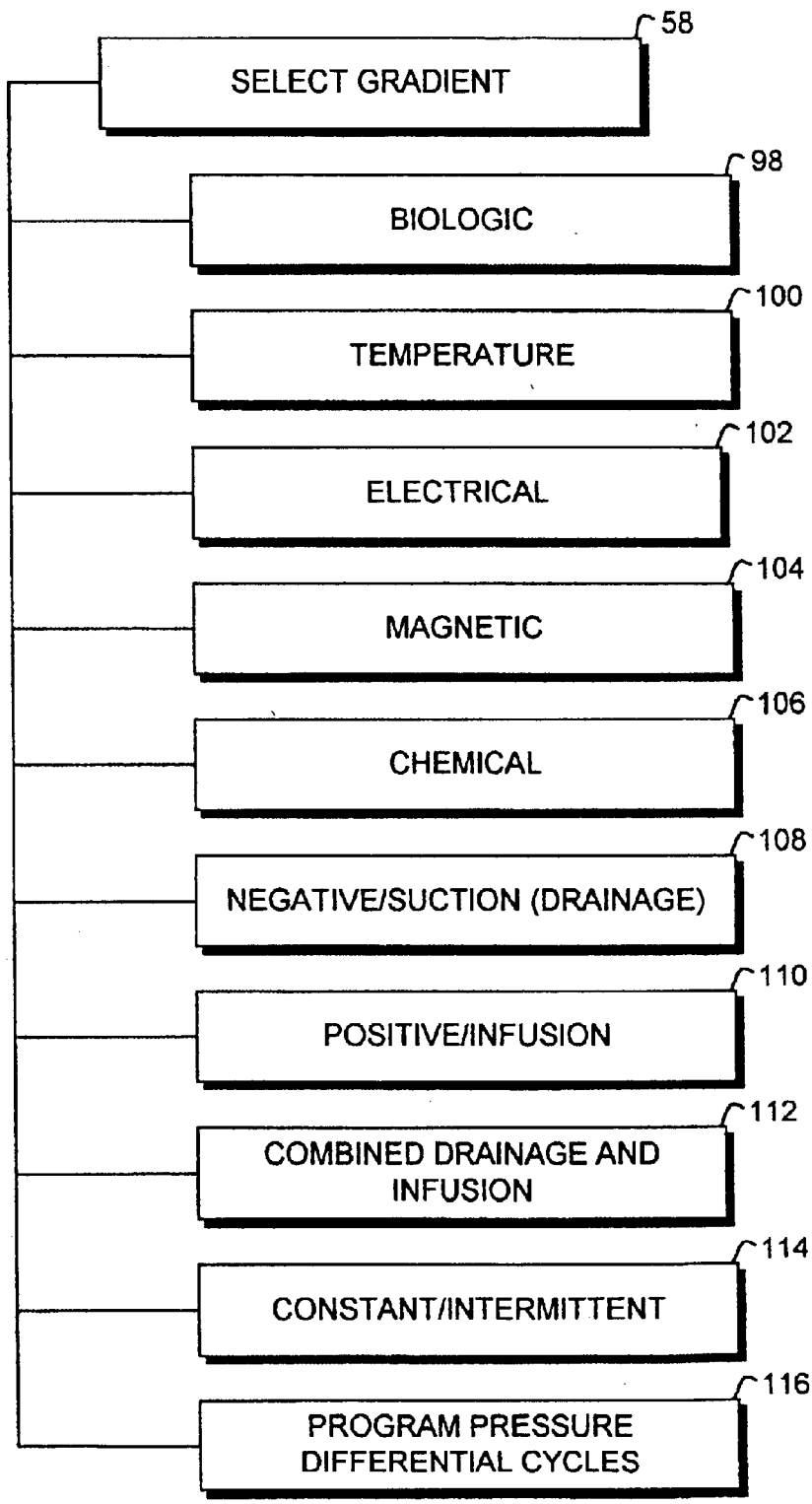
FIG. 6 is an outline of a subprocedure of the treatment method, which subprocedure involves selecting a gradient source.

FIG. 6 shows the subprocedure 58 for selecting the gradient. As shown, biologic 98, temperature 100, electrical 102, magnetic 104 and chemical 106 gradients can be utilized. A negative/suction pressure differential 108 can be utilized to drain the situs 4 and a positive/infusion pressure differential 110 functions to input various fluids and agents to the situs 4. Drainage and infusion can be combined at 112. These functions and operational modes can be sequenced for constant/intermittent operation (114) and can operate simultaneously. They can also be preprogrammed (116) with the controller 10. For example, the gradient source 8 can pause in its operation and provide a substantially static pressure or other condition across the interface 6.

Figure 7:
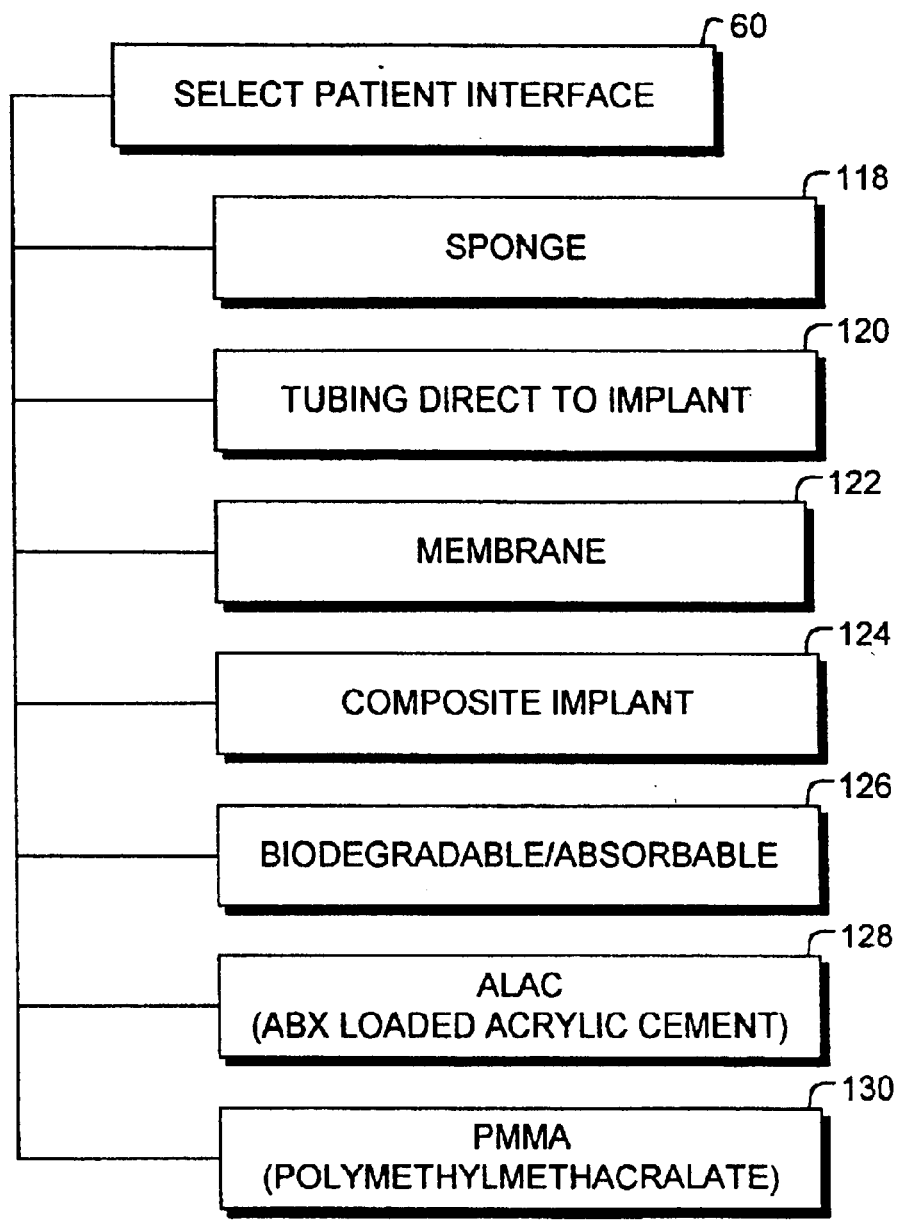
FIG. 7 is an outline of a subprocedure of the treatment method, which subprocedure involves selecting a patient interface.

FIG. 7 shows a subprocedure 60 for selecting the patient interface 6. A hydrophilic or hydrophobic sponge 118 can be placed on the implant porous material portion 28. Alternatively, it can directly receive a tube connected to the gradient source 5 (120). Membranes of porous, semipermeable and impervious material can be utilized (122). As discussed above, the interface 6 can comprise multiple materials in a composite construction (124). Some or all the components of the interface 6 can be biodegradable and absorbable (126). The ALAC acronym identifies antibiotic or antimicrobial (ABX) loaded acrylic cement, which can also be utilized for installing the patient interface 6 (128). Polymethylmethacralate (PMMA) is another adhesive adapted for orthopedic applications, and can be used for adhering one or more of the components of the system 2 to a patient (130).

Figure 8:
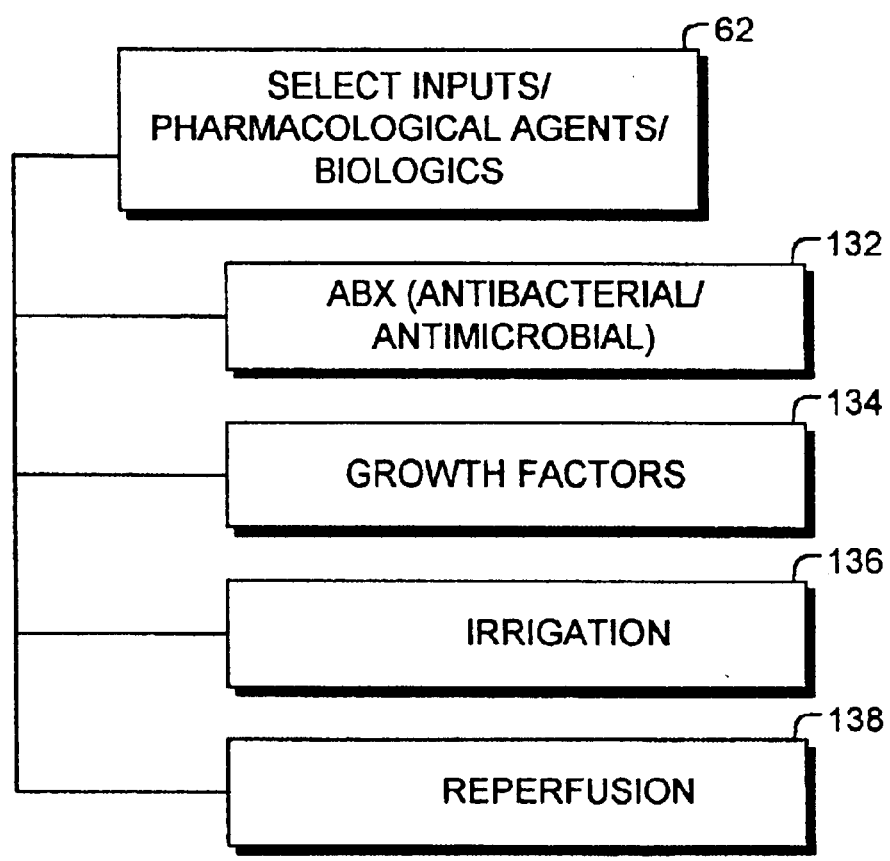
FIG. 8 is an outline of a subprocedure of the treatment method, which subprocedure involves selecting inputs/pharmacological agents/biologics.

FIG. 8 shows the subprocedure 62 for selecting inputs/ pharmacological agents/biologics, which are chosen to enhance healing, counter infection, etc. They can include antibacterial/antimicrobial agents (ABX) 132, growth factors 134, irrigation 136 (i.e., in conjunction with drainage of the situs 4) and reperfusion 138 of the patient's fluids and biologics.

Figure 9:
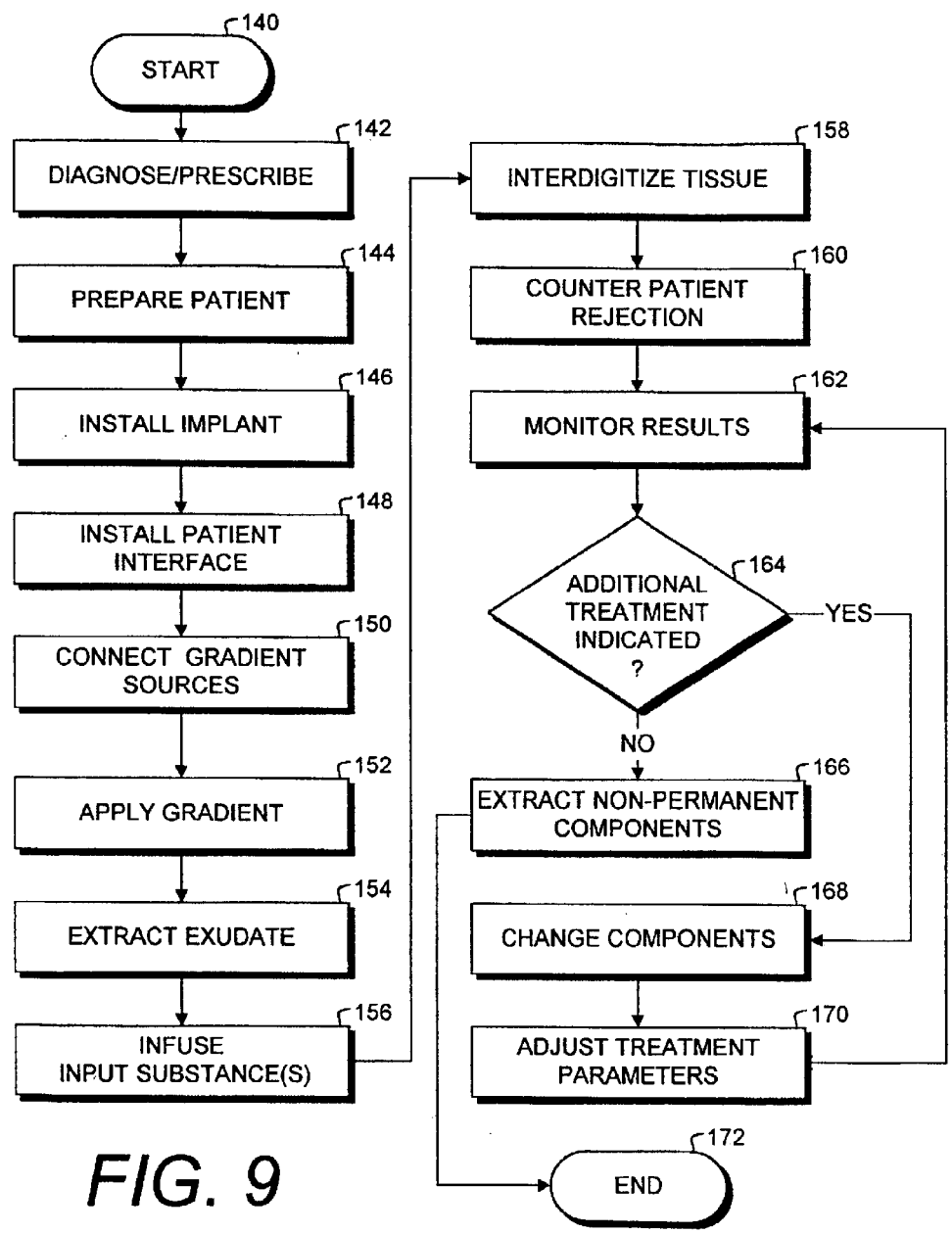
FIG. 9 is a flowchart showing a treatment subprocedure.

FIG. 9 shows a treatment subprocedure 64 starting at 140 and including a diagnosis and prescription of a treatment protocol (142). Following suitable preparations at 144, the implant is installed at 146 and the patient interface is installed at 148. A gradient source(s) is connected at 150 and a gradient is applied at 152. In a negative pressure differential/extraction mode, exudate is extracted at 154. The negative pressure differential/extraction mode also encourages tissue interdigitation (158) for biointegration of the interface 6 into the patient's tissue. In a positive pressure differential input/supply mode, input substances are infused at 156 into the patient interface 6 for distribution by the porous component 28. Various treatments and pharmacologicals are available for countering patient rejection of tissue transplants, and can be used in conjunction with the system 2 at 160. The treatment results can be monitored at 162 through various sensors 11 associated with the monitor/ display 12, and through conventional medical inspections and observations. Components of the system 2 can be changed if additional treatment is indicated at 164, and treatment parameters can be adjusted as indicated for optimum healing at 170 and components can be changed at 168. Finally, non-permanent components can be extracted at 166 and the treatment ends at 172.

Figure 10A:
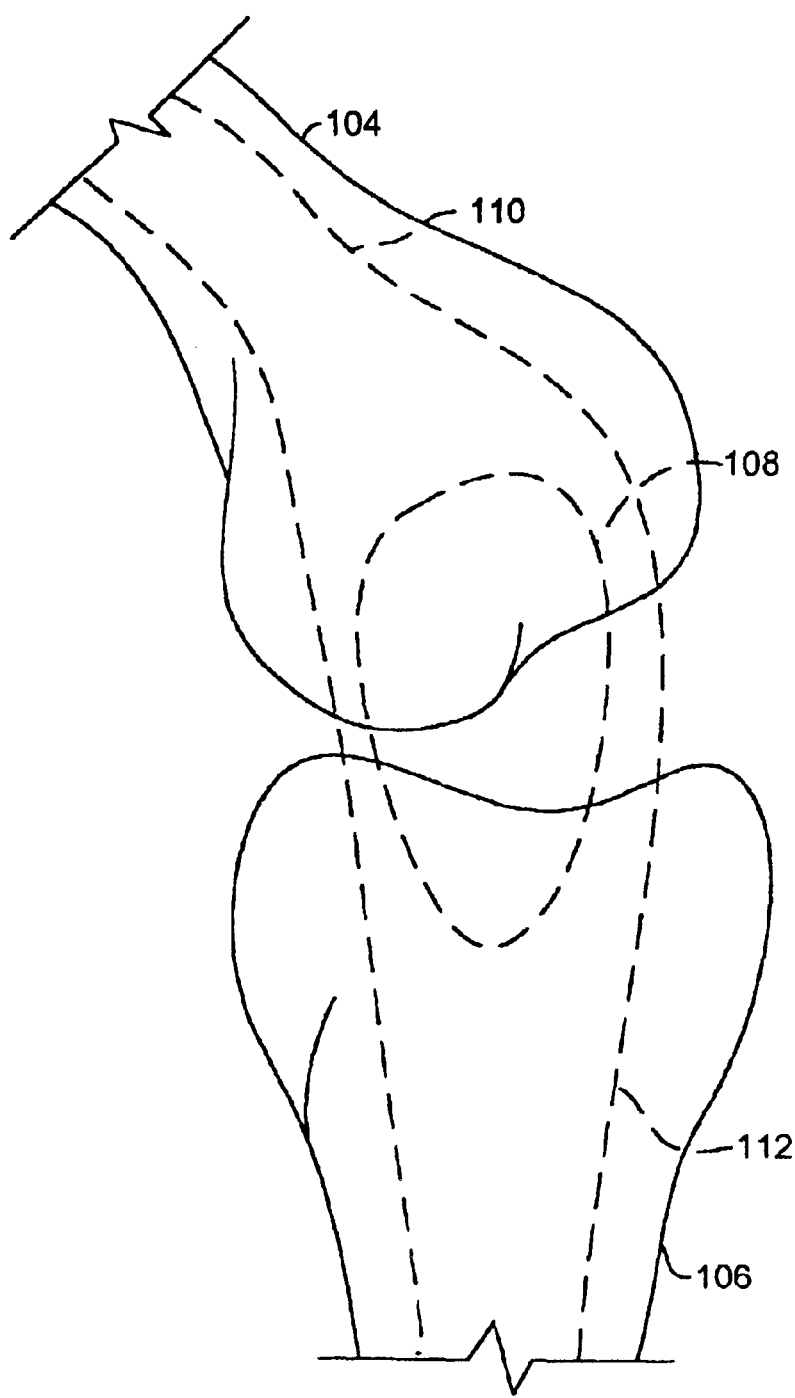
FIG. 10a is a front, right side perspective view of a knee joint.
Figure 10B:
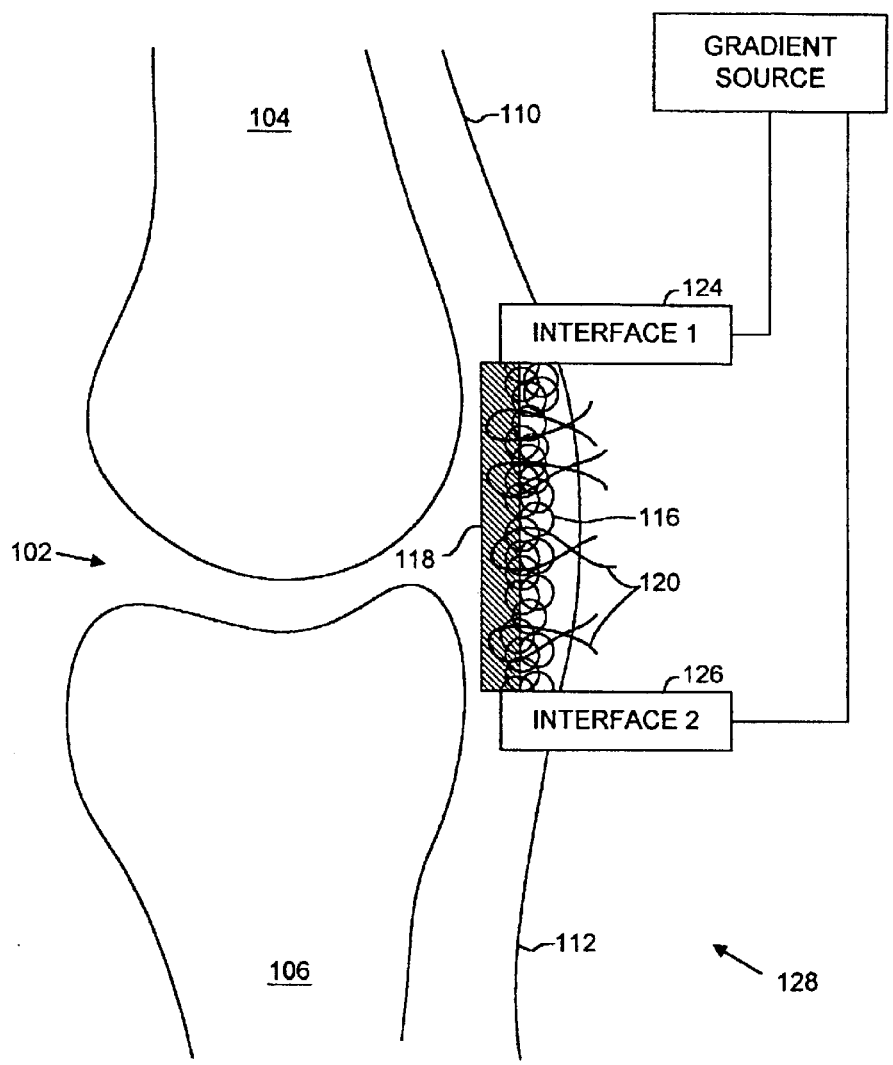
FIG. 10b is a cross-sectional view of the knee joint, showing the porous implant system applied to the patella.

FIG. 10a shows a knee joint 102, a femur 104 and a tibia 106. A patella 108 (kneecap) is connected to a quadriceps tendon 110 and and a patella tendon 112. FIG. 10b shows an implant 114, which includes a porous, outer layer 116. The implant 114 can comprise trabecular metal, porous thermoplastic and other porous materials, as described above. The implant 114 also includes an ultra high molecular weight plastic (UHMWP) inner layer 118 adapted for sliding with respect to the components of the knee joint 102 and providing a relatively low coefficient of friction. The implant 114 is temporarily secured to the tendons 110, 112 by sutures 120, which can be absorbable. The porous outer layer 116 of the implant 114 receives tissue ingrowth, as described above, for permanent bonding. A gradient source 122 is connected to the implant 114 via first and second interfaces 124, 126. The resulting system 128 provides drainage, irrigation, biologic application and other functions, as discussed above.

FIG. 11 shows a system 132 for reconstructing a tibia 134. Damaged tibia tend to have high risks of infection, whereby drainage and the application of various antibiotics, antimicrobials and other biologics comprise important aspects of effective treatment. The system 132 includes a porous implant 136 connected to a gradient source 138 by first and second interfaces 140, 142.

It will be appreciated that various other medical, dental and veterinary applications of the porous implant system and treatment methodology fall within the scope of the present invention. While certain forms of the present invention have been illustrated and described herein, it is not to be limited to the specific forms or arrangement of parts described and shown.

Having thus described the invention, what is claimed as new and desired to be secured by Letters Patent is:

1. A porous implant gradient system for a hard or soft tissue situs, which comprises:
   an implant comprising a porous material adapted to receive tissue ingrowth at the patient situs;
   a gradient source adapted for creating a gradient across at least a portion of the implant;
   a gradient transfer connected to the gradient source and adapted for transferring the gradient; and
   an interface connected to the gradient transfer and to the implant, the interface being adapted to apply the gradient to the portion of the implant across which same is created.

2. The system according to claim 1, which includes:
a controller connected to the gradient source and adapted for controlling application of the gradient.

3. The system according to claim 1 wherein said gradient comprises at least one from the following group of gradients:
biologic; temperature; electrical; magnetic; chemical; negative pressure/suction; and positive pressure/infusion.

4. The system according to claim 1 wherein said porous implant material comprises trabecular metal.

5. The system according to claim 1 wherein said porous implant material comprises thermoplastic.

6. The system according to claim 1, which includes:
said gradient source including a pump adapted for creating a negative pressure differential across said implant;
said negative pressure differential facilitating the ingrowth of surrounding tissue into said implant porous material; and
a collection receptacle connected to said the interface and adapted for receiving exudate from said implant.

7. The system according to claim 6, which includes:
said pump being adapted for creating a positive pressure differential across said implant; and
an input source for an input substance comprising at least one from the following group: irrigation fluid; biologic; antibiotic; antimicrobial; growth factor; and reperfusion.

8. The system according to claim 1 wherein said porous material is biodegradable/absorbable.

9. The system according to claim 1 wherein said implant comprises a composite construction consisting of a porous material portion and a polymeric portion bonded thereto, said polymeric portion comprising a polymeric material with a relatively low coefficient of friction.

10. The system according to claim 1 wherein said implant is bonded to the patient at the situs by a biocompatible adhesive.

11. A method of treating a patient, which comprises the steps of:
diagnosing the patient's condition and prescribing a treatment protocol therefor;
providing an implant with a porous material portion chosen for compatibility with the patient situs;
installing said implant at the situs;
providing a gradient source adapted for creating a gradient across said implant;
connecting the gradient source to the implant;
transferring the gradient from the gradient source to the implant; and
facilitating tissue ingrowth into said implant porous material by said gradient.

12. The method according to claim 11, which includes the additional step of selecting at least one gradient from among the group consisting of: biologic; temperature; electrical; magnetic; chemical; negative/suction (drainage); and positive/infusion.

13. The method in according to claim 11, which includes the additional step of applying the implant in connection with a procedure from among the group consisting of: soft tissue repair; orthopedic reconstruction; tendon attachment; subcutaneous tissue closure; hip replacement; shoulder replacement; elbow replacement; patella replacement; tibia reconstruction; dental; and veterinary.

14. The method according to claim 11, which includes the additional steps of fabricating said porous portion of said implant from a biodegradable/absorbable material and absorbing same within said patient at said situs.

15. The method according to claim 11, which includes the additional steps of:
providing said gradient source with a pump;
providing a negative pressure differential across said porous portion of said implant with said pump;
facilitating tissue ingrowth into said implant porous portion with said negative pressure differential; and
draining said situs with said negative pressure differential.

16. The method according to claim 11, which includes the additional steps of:
providing said gradient source with a pump;
providing a source for an input from among the group consisting of biologic agents; pharmacologic agents; antibiotics; antimicrobials; growth factors; irrigation; and reperfusion;
connecting said pump to said interface;
providing a positive pressure differential across said porous portion of said implant with said pump; and
infusing said situs with said input.

17. The method according to claim 11, which includes additional steps of:
applying a biocompatible adhesive to said implant; and
bonding said implant to the patient's tissue at said situs with said adhesive.

18. The method according to claim 11, which includes additional step of providing a composite implant construction with a porous material portion and a polymeric portion bonded thereto, said polymeric portion comprising a material with a relatively low coefficient of friction.

19. The method according to claim 11, which includes the additional steps of:
providing a programmable controller connected to said gradient source;
programming said controller for operation of said gradient source pursuant to a treatment protocol;
operating said gradient source by said controller pursuant to said treatment protocol;
connecting a monitor to said controller; and
displaying data concerning said treatment progress on said monitor.

20. A method of treating a patient condition involving first and second tissue portions located at a situs within the patient's body, which method comprises the steps of:
diagnosing the patient's condition;
prescribing a treatment protocol;
providing a programmable controller;
programming the controller pursuant to the treatment protocol;
providing a monitor;
connecting the monitor to the controller and displaying data concerning the treatment status on the monitor;
providing an implant with a composite construction consisting of a porous material portion and a polymeric portion bonded thereto, the latter having a relatively low coefficient of friction;
providing a gradient source;
connecting the gradient source to the controller and controlling the operation of the gradient source with the controller;
providing an interface and connecting same to said gradient source and said implant;

providing a sense or and connecting same to one of said patient at said patient situs or said gradient source, into said controller;

sensing a patient condition or status of said treatment with said sensor, relaying same to said controller and displaying data concerning same on said monitor;

applying said gradient to said porous portion of said implant;

drawing issue date from said the implant through said interface and collecting same; and providing an input source;

infusing said implant with input material from said input source through said interface.

* * * * *